(12) United States Patent
Liste et al.

(10) Patent No.: US 7,458,944 B2
(45) Date of Patent: Dec. 2, 2008

(54) COSMETIC CLEANING PRODUCT

(75) Inventors: Kathrin Liste, Hamburg (DE); Olaf Rhode, Elmshorn (DE); Jens Treu, Norderstedt (DE)

(73) Assignee: Beiersdorf AG, Hamburg (DE)

( * ) Notice: Subject to any disclaimer, the term of this patent is extended or adjusted under 35 U.S.C. 154(b) by 570 days.

(21) Appl. No.: 10/818,583

(22) Filed: Apr. 5, 2004

(65) Prior Publication Data

US 2004/0267170 A1 Dec. 30, 2004

Related U.S. Application Data

(63) Continuation of application No. PCT/EP02/10928, filed on Sep. 30, 2002.

(30) Foreign Application Priority Data

Oct. 4, 2001 (DE) ................. 101 48 933

(51) Int. Cl.
  *A61H 15/02* (2006.01)
(52) U.S. Cl. .................... 601/17; 601/137
(58) Field of Classification Search ......... 601/134–138, 601/17; 401/6, 183
  See application file for complete search history.

(56) References Cited

U.S. PATENT DOCUMENTS

| 1,594,636 | A |   | 8/1926  | Smith     |         |
|-----------|---|---|---------|-----------|---------|
| 2,584,735 | A | * | 2/1952  | Pancoast  | 401/26  |
| 3,892,829 | A |   | 7/1975  | Uhlig     |         |
| 4,199,129 | A |   | 4/1980  | Fischer   |         |
| 4,485,807 | A |   | 12/1984 | Guerèt    |         |
| 4,775,256 | A | * | 10/1988 | Roth      | 401/28  |
| 4,811,726 | A |   | 3/1989  | Goncalves et al. |  |
| 4,823,777 | A |   | 4/1989  | Goncalves et al. |  |
| 4,900,504 | A |   | 2/1990  | Fischer   |         |
| 5,125,423 | A |   | 6/1992  | Butterbrodt |       |
| 5,445,596 | A |   | 8/1995  | Grace     |         |
| 5,766,210 | A | * | 6/1998  | Komoroczy et al. | 601/135 |

(Continued)

FOREIGN PATENT DOCUMENTS

DE    30 09 587 A1    9/1981

(Continued)

OTHER PUBLICATIONS

International Search Report from corresponding International Application No. PCT/EP02/10951 dated Mar. 4, 2003.
German Search Report dated Aug. 29, 2002.

*Primary Examiner*—Michael A. Brown
(74) *Attorney, Agent, or Firm*—Greenblum & Bernstein, P.L.C.

(57) ABSTRACT

The invention is a cosmetic cleaning product, comprising a massage applicator comprising a container body and a massage device having at least one massage pin device, the pin device having at least one first surface which is configured to be in contact with the surface to be massaged, wherein a force can be transmitted between the first surface of the massage pin device and the surface to be massaged, and wherein at least one predetermined massage characteristic feature selected from the group consisting of a predetermined hardness, a predetermined geometry and a predetermined elasticity exists in a region of the first surface of the massage pin device which is configured to be in contact with the surface to be massaged, and at least one adjusting device which can adjust the at least one predetermined massage characteristic feature, and a cosmetic cleaning formulation.

24 Claims, 2 Drawing Sheets

U.S. PATENT DOCUMENTS

| | | | |
|---|---|---|---|
| 6,129,469 | A | 10/2000 | Messer et al. |
| 6,379,680 | B2 | 4/2002 | Gers-Barlag et al. |
| 6,703,427 | B2 | 3/2004 | Schmucker et al. |
| 2002/0018789 | A1 | 2/2002 | Gers-Barlag et al. |
| 2002/0054861 | A1 | 5/2002 | Schmucker et al. |
| 2002/0172540 | A1 * | 11/2002 | Hauser et al. .................. 401/6 |

FOREIGN PATENT DOCUMENTS

| | | |
|---|---|---|
| DE | 35 26 109 A1 | 1/1987 |
| DE | 37 08 051 A1 | 9/1987 |
| EP | 05 05 724 A2 | 9/1992 |
| EP | 0 688 658 A2 | 12/1995 |
| EP | 1153592 * | 4/2001 |
| GB | 643633 | 9/1950 |
| JP | 11 276250 A | 10/1999 |

* cited by examiner

COSMETIC CLEANING PRODUCT

CROSS-REFERENCE TO RELATED APPLICATIONS

This is a continuation application of PCT/EP02/10928, filed Sep. 30, 2002, which is incorporated herein by reference in its entirety, and also claims the benefit of German Priority Application No. 101 48 933.1, filed Oct. 4, 2001.

FIELD OF THE INVENTION

The present invention relates to a cosmetic cleaning product comprising a container for a cosmetic cleaning formulation, a massage device and a cosmetic cleaning formulation. The massage device and container are firmly connected to one another and are called the packing means in the following text. The firm connection of the massage head and container can also be constructed such that the connection can be separated for the purpose of topping up. A specific use of the cosmetic cleaning formulation is a shower product matched specifically to the massage device.

BACKGROUND OF THE INVENTION

Containers—such as, for example, bottles or jars, serve inter alia as a storage location for liquids in the cosmetics and dermatological sector. The bottles here are produced in particular from a flexible plastic, so that gentle pressure on the body of the bottle is sufficient to expel the liquid in the bottle out of the opening.

The known plastic bottles for shower formulations, liquid soaps and shampoo may be mentioned by way of example here, without this list being complete. Bottles which can be closed with a screw lid are preferred.

The bottles or containers are often produced by the extrusion blow molding process.

U.S. Pat. No. 3,892,829 discloses a process and a device for the production of flat bottles from an extruded parison which is preblown in an intermediate mold and only then is transferred into a final blow mold, the mold cavity of which has the contour of the flat bottle to be produced.

DE 37 02 844 A1 discloses a process which follows this principle and an extrusion blow molding machine which operates thereby. In this, a parison of plastic is freely extruded, taken up in an intermediate mold and blow-molded there into a rotationally symmetric intermediate molding. This intermediate molding, which consequently has a circular cross-section at every height, already has approximately the length (height) of the flat bottle to be produced, and has in its main sections (base, body, neck) a circumference which is more or less approximately the corresponding circumferences of the flat bottle. The latter is shaped by transferring the intermediate molding into a final blow mold, such as is known, for example, from DE 27 20 448 C2.

This technique of production, which is largely waste-free and accordingly free from pinch-off welds, of flat bottles of substantially uniform wall thickness has proved itself.

In EP 0 688 658 A1, the intermediate molding is supported (mechanically) from underneath at least during transfer from the intermediate mold into the final blow mold. The intermediate molding is supported by an additional movable mold part at least during transfer from the intermediate mold into the final blow mold. This mold part can advantageously match the base contour of the intermediate molding. As a rule the molding must be displaceable in the vertical direction, so that closing of the final blow mold is not impeded.

Massage applicators have also be known for a long time. They exist in the most diverse shapes and materials. They can be made of plastics or naturally occurring materials.

A massage device which can be controlled electrically and is integrated into seating furniture, such as an easy chair or the like, is already known. In this known massage device one or more massage heads are arranged underneath the seat cover. These massage heads are driven electrically by electric motors, so that they are set in motion and a person sitting on the seating furniture can be massaged in an appropriate place by means of the massage head.

A massage device in which massage pins extend from a ball of plastic distributed in the radial direction over the ball surface, so that for massage this ball can be rolled over the surface to be massaged or the human body is furthermore known.

Plastic massage applicators can have the most diverse shapes. Roller/ball applicators and pin applicators are known.

In roller or ball applicators movable balls are held in a suitable direction and a pure pressure massage is achieved in this manner. The pressure massage is very skin-friendly since the frictional resistance is reduced to a minimum.

Pin applicators of rubber or flexible plastic show an increased friction. This increased friction intensifies the massage effect in the upper layers of skin, but can also lead to skin irritations on sensitive areas of skin. Generally, a more intense massage effect is achieved by massage with a pin applicator. At the same time massage with a pin applicator also leads to higher mechanical stress on the skin and the underlying tissue and therefore to an increased blood circulation in the skin.

The increased blood circulation and the massage of the subcutaneous tissue leads to a consolidation of the subcutaneous tissue. This consolidation leads to an improvement in the appearance of the skin and in this way prevents cellulite or counteracts it.

The points mentioned for massage applicators of plastic also apply generally to massage applicators of naturally occurring materials, such as, for example, wood. However, in the case of these applicators of naturally occurring substances there are also additionally special forms which are made of, for example, braided sisal rope or similar materials. On these applicators the rough surface of the naturally occurring substances is used for the massage.

Even in a simple water bath without addition of surfactants a swelling of the horny layer of the skin initially occurs, the degree of this swelling depending, for example, on the duration of the bath and its temperature. At the same time water-soluble substances, e.g. water-soluble dirt constituents, but also endogenous substances of the skin which are responsible for the water-binding capacity of the horny layer, are washed off or out. In addition, skin oils are dissolved and washed out to a certain extent by endogenous surface-active substances of the skin. After initial swelling, this causes a subsequent significant drying out of the skin, which can be intensified further by wash-active substances.

In healthy skin these processes are in general inconsequential, since the protective mechanisms of the skin can easily compensate such mild disturbances in the upper layers of skin. However, already in the case of non-pathological deviations from the normal state, e.g. due to environment-related wear damage or irritation, damage caused by light, senile skin etc., the protective mechanism of the skin surface is impaired. Under certain circumstances it is then no longer capable of fulfilling its task by its own means and must be regenerated by external measures.

Liquid shower preparations in the form of syndets (synthetic detergents) have been known for a long time. They are substantially surface-active substances or substance mixtures which are offered to the user in various formulations. Formulations of such a type are in general distinguished by a more or less high water content, but can also be in the form of, for example, a concentrate. Nowadays these are chiefly soap-free formulations with a pH of below 7. The development of such products was first possible with the discovery of synthetic surfactants. Since this time these products have been frequently further developed and there is a very large field of the prior art. These wash-active substances have, as is known to the expert, barrier-damaging actions. Due to the prolonged application more surfactants also remain on the skin after rinsing off with water. The barrier-damaging action of surfactants and the remaining on the skin after rinsing off has already been described in detail in our Application "Process for the preparation of particularly skin-friendly cosmetic or dermatological cleaning formulations" (DE 199 60 767 A1). In particular, the intensive application of the shower product by means of massage leads to an increased risk of irritation. The top layers of skin are detached by the massage and the skin barrier weakened. As a result, the wash-active substances can penetrate into lower layers of skin and cause irritation.

The fluid formulations are preferably emulsions, suspensions, colloids, dispersions gels or solutions.

Gelatinous shower formulations can also be formulated without gel-forming agents, since certain surfactant mixtures thicken on addition of salts.

In the technical sense, gels are understood as: relatively dimensionally stable, easily deformable disperse systems of at least two components, which as a rule comprise a—usually solid—colloidally divided substance of long-chain molecular groupings (e.g. gelatins, silica, polysaccharides) as the structure-forming substance and a liquid dispersing agent (e.g. water). The colloidally divided substance is often called a thickener or gelling agent. It forms a three-dimensional network in the dispersing agent, it being possible for individual particles present in colloidal form to be linked to one another more or less firmly via electrostatic interaction. The dispersing agent, which surrounds the network, is distinguished by an electrostatic affinity for the gelling agent, i.e. a predominantly polar (in particular: hydrophilic) gelling agent preferably gels a polar dispersing agent (in particular: water), whereas a predominantly non-polar gelling agent preferably gels non-polar dispersing agents.

Strong electrostatic interactions, which are realized, for example, in hydrogen bridge bonds between the gelling agent and dispersing agent, but also between dispersing agent molecules among one another, can lead to high crosslinking also of the dispersing agent. Hydrogels can comprise almost 100% water (in addition, for example, to approximately 0.2-1.0% of a gelling agent) and thereby entirely have a solid consistency. The water content here is present in ice-like structural elements.

In the field of cosmetics and pharmaceuticals formulation, lipogels and oleogels (from waxes, fats and fatty oils) and carbogels (from paraffin or petrolatum) are furthermore also usual. In practice, a distinction is made between oleogels, which are in a practically anhydrous form, and hydrogels, which are practically fat-free. Gels are usually transparent. In the field of cosmetics or pharmaceuticals formulation, gels are as a general rule distinguished by a semi-solid, often fluid consistency.

So-called surfactant gels are furthermore conventional formulations of the prior art. These are understood as meaning systems which, in addition to water, have a high concentration of emulsifiers, typically more than approximately 25 wt. %, based on the total composition. If oil components are solubilized in these surfactant gels, microemulsion gels, which are also called "ringing gels" are obtained. Cosmetically more elegant microemulsion gels can be obtained by addition of nonionic emulsifiers, for example alkyl polyglycosides.

Emulsions are metastable two- or multiphase systems in which the individual phases are present in the liquid state. The most usual emulsions are O/W (oil-in-water) and W/O (water-in-oil) emulsions. Rarer presentation forms are multiple emulsions, that is to say those which in the droplets of the dispersed (or discontinuous) phase in their turn contain droplets of a further dispersed phase, e.g. W/O/W emulsions and O/W/O emulsions. In simple emulsions, in the one phase finely disperse droplets of the second phase enclosed by an emulsifier shell (water droplets in a W/O emulsions or lipid vesicles in O/W emulsions) are present. The droplet diameters of the usual emulsions are in the range from approximately 1 µm to approximately 50 µm. Such "macroemulsions" are, without further coloring additives, milky white in color and opaque. Finer "macroemulsions", the droplet diameters of which lie in the range from approximately $10^{-1}$ µm to approximately 1 µm, are, again without coloring additives, bluish-white in color and non-transparent.

Micellar and molecular solutions with particle diameters of less than approximately $10^{-2}$ µm appear clear and transparent.

The droplet diameter of transparent or translucent microemulsions, on the other hand, is in the range from about $10^{-2}$ µm to about $10^{-1}$ µm. Such microemulsions are usually low-viscosity. The viscosity of many microemulsions of the O/W type is comparable to that of water.

Emulsions represent by far the most important product type in the field of skin care compositions or in the field of cosmetic and/or dermatological formulations. Emulsions are disperse two- or multiphase systems, cosmetic emulsions comprising at least one fatty phase (fats and mineral oils, fatty acid esters, fatty alcohols etc.) and at least one aqueous phase (water, glycerol, glycols etc.) which are distributed in one another in the form of very fine droplets with the aid of emulsifiers. If the two liquids are water and oil and oil droplets are present finely divided in water, this is an oil-in-water emulsion (O/W emulsion, for example milk). The basic character of an O/W emulsion is imposed by the water. In a water-in-oil emulsion (W/O emulsion, for example butter) the principle is the reverse, the basic character here being determined by the oil.

The oily phase is advantageously chosen from the group of esters of saturated and/or unsaturated, branched and/or unbranched alkanecarboxylic acids and saturated and/or unsaturated, branched and/or unbranched alcohols, from the group of esters of aromatic carboxylic acids and saturated and/or unsaturated, branched and/or unsaturated alcohols, from the group of branched and unbranched hydrocarbons and waxes, silicone oils, dialkyl ethers, the group of saturated or unsaturated, branched or unbranched alcohols, and fatty acid triglycerides. Any desired blends of such oil and wax components can also advantageously be employed in the context of the present invention. It may also be advantageous, where appropriate, to employ waxes, for example cetyl palmitate, as the sole lipid component of the oily phase.

The oily phase can advantageously have a content of cyclic or linear silicone oils, for example cyclomethicone (octamethylcyclotetrasiloxane) or consist entirely of such oils, although it is preferable to use an additional content of other oily phase components in addition to the silicone oil or the silicone oils. The emulsions described here and in the following can thus correspondingly be produced as silicone emulsions with use in part or entirely of silicone oils. Corresponding statements apply to the other oil-containing formulations.

The expert knows of a large number of possibilities for formulating stable O/W formulations for cosmetic or dermatological use, for example in the form of creams and ointments which are spreadable in the range from room to skin temperature, or as lotions and milk, which are rather fluid in this temperature range and can be stored particularly favorably with the containers according to the invention.

The stability of emulsions depends inter alia on their viscosity, in particular on the viscosity of the external phase. An emulsion becomes unstable if the finely dispersed particles agglomerate again into larger aggregates and the droplets which touch each other merge. This process is called coalescence. The process of coalescence proceeds more slowly the more viscous the external phase of the emulsion.

O/W emulsions are accordingly as a rule stabilized by thickeners, which increase the viscosity of the aqueous phase. Polyacrylates (Carbomer) and further organic thickeners, for example, are suitable for this. A disadvantage of this method of improving the stability is the sensitivity of these formulations to electrolytes. Furthermore, chiefly higher-viscosity formulations (such as creams or ointments) are of course to be prepared in this manner.

Emulsions of "liquid" (=fluid) consistency are used in cosmetics for example as a care, cleaning, facial or hand lotion. As a rule, they have a viscosity of about 2,000 mPa·s up to about 10,000 mPa·s. Particular attention is to be paid to the stability of fluid emulsions, since the considerably higher mobility of the particles promotes a faster coalescence.

Conventional emulsifiers can be classified into ionic (anionic, cationic and amphoteric) and nonionic according to their hydrophilic molecular part: The best-known example of an anionic emulsifier is the soaps, as the water-soluble sodium or potassium salts of saturated and unsaturated higher fatty acids are usually called.

Important representatives of the cationic emulsifiers are the quaternary ammonium compounds.

The hydrophilic molecular part of nonionic emulsifiers often consists of glycerol, polyglycerol, sorbitans, carbohydrates or polyoxyethylene glycols and is usually linked to the lipophilic molecular part via ester and ether bonds. This usually consists of fatty alcohols, fatty acids or iso-fatty acids. The lipophilicity and hydrophilicity of emulsifiers can be varied within wide limits by varying the structure and the size of the polar and the nonpolar molecular part.

The correct choice of the emulsifiers is decisive for the stability of an emulsion. The characteristics of all the substances contained in the system are to be taken into consideration here. Considering skin care emulsions, for example, polar oily components and, for example, UV filters lead to instabilities. In addition to the emulsifiers, other stabilizers are therefore also used, these for example increasing the viscosity of the emulsion and/or acting as a protective colloid.

The use of the conventional emulsifiers in cosmetic or dermatological formulations is acceptable per se. Nevertheless, emulsifiers, as in the end any chemical substance, can cause allergic reactions or reactions based on hypersensitivity of the user in the individual case. There has therefore been no lack of attempts to reduced the amount of conventional emulsifiers to a minimum, and in the ideal case even completely.

A reduction in the amount of emulsifier required can be achieved, for example, if the fact that very finely divided solid particles have an additional stabilizing action is utilized. This results in a concentration of the solid substance at the oil/water phase boundary in the form of a layer, whereby merging of the disperse phases is prevented. It is not the chemical but the surface properties of the solid particles which are of essential importance here.

It is a relatively new technical development to stabilize cosmetic or dermatological formulations only by very finely divided solid particles. Such "emulsifier-free" emulsions are called Pickering emulsion after their inventor. One possibility of carrying out stabilization of solids in a cosmetic or dermatological formulation is, for example according to May-Alert (Pharmazie in unserer Zeit, vol. 15, 1986, no. 1, 1-7), to use emulsifier mixtures which comprise both anionic and cationic surfactants. Since insoluble, electroneutral compounds always precipitate out when anionic and cationic surfactants are brought together, an additional stabilization of solids in the sense of a Pickering emulsion can be achieved by controlled precipitation of these neutral surfactants in the oil/water interface.

WO 98/42301 A1 furthermore describes emulsifier-free finely disperse systems of the water-in-oil type which are stabilized by the addition of micronized, inorganic pigments chosen from the group of metal oxides, in particular titanium dioxide.

Emulsifier-free preparations based on so-called hydrodispersions have been accessible for the user for some time. Hydrodispersions are dispersions of a liquid, semi-solid or solid internal (discontinuous) lipid phase in an external aqueous (continuous) phase.

In contrast to O/W emulsions, which are distinguished by a similar phase arrangement, hydrodispersions however are substantially free from emulsifiers. Hydrodispersions, like emulsions, are metastable systems and tend to transform into a state of two discrete phases which are in themselves cohesive. In emulsions, the choice of a suitable emulsifier prevents phase separation.

In hydrodispersions of a liquid lipid phase in an external aqueous phase, the stability of such a system can be ensured, for example, by building up a gel structure, in which the lipid droplets are suspended in a stable manner, in the aqueous phase.

W/O lipodispersions are, in converse analogy, emulsifier-free finely disperse formulations of the water-in-oil type.

When a standard shower product was used with one of the abovementioned applicators the following negative product properties occurred in the past:

Shower product and massage applicator were not matched to one another, too intense or too weak a massage effect was achieved.

The intensity of the massage was not variable and therefore could not be adjusted to various skin zones.

The long action time of the shower product during the massage led to skin irritation.

Applicator was not matched to the shower product. Possibly, the applicator could be cleaned only poorly or not at all, or the surface was attacked or decomposed by the shower product.

Applicator and shower product were not matched to one another so that microbial contamination of the shower product and applicator could occur during inappropriate handling.

A standard shower product and one or the abovementioned applicators always had to be used hitherto for a massage by means of an applicator under the shower, to date specific massage shower products have not yet been disclosed.

SUMMARY OF THE INVENTION

The object of the invention is to provide a container which offers an optimum connection between a storage location and a massage device, so that separation of the two functions into two separate devices is no longer necessary. Furthermore, suitable shower product formulations had to be found specifically for this use.

This object is achieved, surprisingly, by a cosmetic cleaning product such as is described in the main claim. The subclaims relate to advantageous embodiments of this cleaning product, in particular its massage applicator and the cosmetic cleaning formulations it contains. The use of such a cleaning product as a shower formulation is furthermore claimed.

Liquid and fluid substances and easily distributable solid substances and mixtures of two or more components can be stored with the container according to the invention, the massage device at the same time facilitating massaging-in of the substances released into the skin.

The container is outstandingly suitable for emulsions, suspensions, dispersions, solutions (gaseous, liquid and solid substances), colloids and the like, very preferably for application of cosmetic or dermatological compositions on to the skin, in particular gels, emulsions, Pickering emulsions, hydrodispersions and lipodispersions.

According to a particular aspect, the invention is based on the object of providing a massage device which is flexible in use and inexpensive to produce.

According to a particular aspect, the invention is based on the object of providing a massage device which causes an individually matched massage effect.

BRIEF DESCRIPTION OF THE DRAWINGS

The packing means is explained in more detail in the following with the aid of the figures, where it is not intended thereby to limit the invention.

DETAILED DESCRIPTION OF THE PREFERRED EMBODIMENTS

Figure 1:
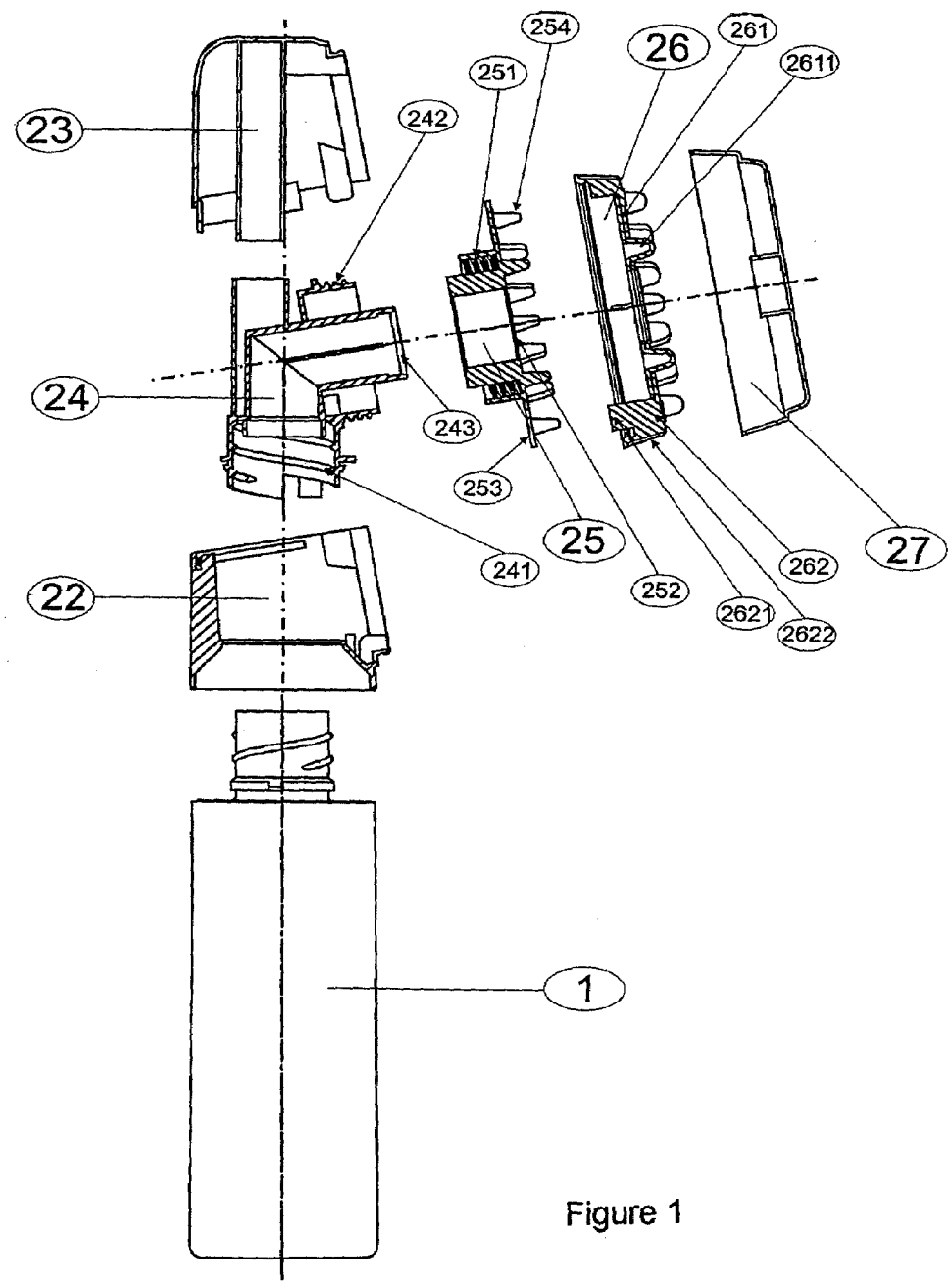
FIG. 1 shows an exploded drawing of a particularly advantageous embodiment of the massage applicator according to the invention, with a particular embodiment of a container in bottle form and several individual parts belonging to the devices (bottle (1), massage device (2) comprising: (22) lower head cap, (23) upper head cap, (24) angle piece with bottle thread (241), massage thread (242) and valve seat (243), (25) massage pin inner part with massage hardness adjustment thread (251) and valve section (252), (26) massage pin outer part comprising a massage pin disc (261) of flexible material and sieve plate with rotating ring (262) of hard material, (27) cover cap) in side view.

According to the invention, a massage device comprises a first surface which, on massaging, is in contact with the surface to be massaged, wherein a predetermined massage characteristic feature can be adjusted by means of an adjusting device.

The massage device according to the invention is constructed in particular such that it comprises a massage pin device with at least one pin and with a first surface which, on massaging, is in contact with the surface to be massaged.

In the context of the present invention, a massage pin device is, in particular, a device which comprises one or more pins, on which the first surface is arranged. In the context of the present invention, the term "pin" is to be interpreted widely and extends in particular to profile elevations of an external contour of this massage pin device. The massage pin device or the pin is also optionally constructed as a substantially non-profiled surface or as a non-elevated surface. Particularly preferably, however, several pins are provided, which extend with a cylindrical external contour or a spherical segment-shaped or hemispherical or triangular or pyramidal or other external contour from one surface of the massage pin device or of a base body.

In the context of the present invention, the surface to be massaged is, in particular, an external surface of the human body, such as the skin of the human body.

During the massage a force is transmitted from the massage device or the massage pin device or the first surface to the surface to be massaged. This force has the effect in particular that the massage of the surface to be massaged can be perceived sensitively.

In the region of the first surface, a predetermined hardness, a predetermined elasticity and/or a predetermined geometry exists. This hardness, elasticity and geometry is determined in particular by the geometry or the material of the component carrying this first surface, of the components adjacent to the component carrying this first surface or the particular relative arrangement to one another.

A massage characteristic feature in the context of the present invention is, in particular, a characteristic feature which at least co-determines the transmission of force and/or energy between the first surface and the surface to be massaged, and indeed in particular in respect of the surface or time distribution of this transmitting force or energy. A massage characteristic feature in the context of the present invention is preferably the hardness, the elasticity or the geometry in the region of the first surface.

In the context of the present invention, the formulation "in the region of the first surface" is to be understood in particular as meaning that the characteristic feature actually given for the first surface or the component carrying this first surface, such as elasticity or hardness or the like, exists, or as meaning to the extent that the corresponding (substitute) characteristic feature is effected at this first surface in interaction with other components.

Such an interaction is explained in the following by way of example, without the intention thereby being to limit the invention.

One or more pins are each constructed as hollow cylinders and have in a first frontal region optionally a rounded-off or semicircular limiting wall on the face, and wherein in the second frontal region opposite the first an opening is provided for accommodation of a mandrel, for example piston-shaped, which can be displaced axially within the pin. The pin is substantially thin-walled in construction and is made of a substantially flexible material. This material has a predetermined elasticity and a predetermined hardness. When the massage device is loaded for massage and a predetermined external surface region of the pin is in contact with the surface to be massaged, the action of a predetermined elasticity of this pin during loading of the surface to be massaged and a particular hardness action exist in particular due to the material and the geometric construction of the pin. This hardness action and elasticity which exist in the region of the first surface can be changed by displacing the piston-shaped internal body axially within the pin, as a result of which detectable characteristic features in the region of the first surface, such as the hardness or the elasticity or the resistance of the pin to kinking or the like, are changed. This action in an embodiment given by way of example is generated in that the rigidity, measurable in the region of the first surface, of the overall device of pins and pistons arranged therein is changed.

This above construction given by way of example and the interaction of the abovementioned various elements of the device according to the invention are not intended to limit the invention. It is preferable that the geometry of the first surface or of a surface adjacent to this first surface can be changed by the interaction of various structural elements.

Particularly preferably, one component is provided with the first surface and is relatively flexible or elastic in construction compared with one or more further components, which are arranged movably relative to the component carrying the first surface and change the geometry of the first surface or a surface adjacent to this first surface during a relative movement.

Preferably, the massage characteristic feature of the massage pin device, such as hardness, elasticity or geometry in the region of the first surface of the massage pin device, is preferably infinitely adjustable. The massage device or the massage pin device or the adjusting device preferably has at least one first element and at least one second element, which are arranged movably relative to one another. In various relative positions of these elements, various massage characteristic features, such as hardness, elasticity and geometry, exist in the region of the first surface of the massage device.

Preferably, the second element is arranged or can be arranged at least partly in the first element or in a depression of the first element. The first element is particularly preferably a replaceable or adjustable attachment which can be mounted or is mounted on at least one second element.

In a particularly preferred embodiment of the invention at least one second element is a replaceable or adjustable insert which can be inserted into at least one second element or which is arranged within at least one second element.

According to a particularly preferred embodiment of the invention, at least one first element is at least partly hollow in construction.

At least one second element preferably has an external surface region on the outside which, under predetermined circumstances, is in contact with an internal surface region, on the inside, of at least one second element. This contact can exist in particular at predetermined or at all relative positions between the first element and the second element, it being possible for the area content of the contacting surface to be constant or variable.

Preferably, at least one first element is arranged axially movably within a second element. This axial mobility is of a construction in particular such that the second element is arranged longitudinally displaceably within the first element.

Particularly preferably, the external contour of at least one second element is provided with an external thread and the internal contour of at least one first element is provided with an internal thread, so that the external thread of the second element can engage in the internal thread of the first element.

According to the invention, it is provided in particular that the first surface of the massage device which, on massaging, is in contact with the surface to be massaged is a surface, such as the external surface, of the first element. At least one first element is, preferably in the region of its external surface, and indeed in particular in the region of the first surface of the massage pin device or the massage device, more flexible in construction than the second element in a predetermined external surface region of this second element. This predetermined external surface region is particularly preferably a surface region which is supported under predetermined circumstances against an internal surface of the first element, and indeed optionally at a predetermined relative position between the first element and the second element in a region of the internal surface of the first element which is assigned to the external surface region of this element described as more flexible.

At least one first element preferably differs from a second element by its material, the first element particularly preferably being made of a more flexible material than the second element.

The first element and the second element are each made of one or of different materials.

Preferably, the first and/or the second element is produced from plastic, such as polyethylene or polypropylene or the like. Particularly preferably, the first and/or the second element is produced from a thermoplastic resin, thermosetting resin or elastomer.

Preferably, the material from which the first element is produced has at least one material characteristic feature which differs from a material characteristic feature of the second element.

Preferably, at least one surface region of the first surface of the massage pin device is constructed in a substantially rounded-off manner.

Preferably, at least one first element is a pin of substantially hollow construction and at least one second element is constructed like a mandrel, where this second element extends or can extend into the hollow space of this pin. The mandrel-like construction of this second element is not intended to limit the invention in respect of the construction of the surface contour of the second element.

In particular, the second element is of longer construction in the direction in which it extends into the pin than in its dimensions of the cross-sectional surface arranged perpendicular to this direction. It is furthermore preferable that the second element is of shorter construction in the abovementioned direction than the dimensions of the said cross-sectional surface.

Particularly preferably, the second element can be inserted into the first element or is adjustable in the first element, to provide different massage characteristic features, such as hardness, elasticity or the like between the first element and the second element in the region of the first surface at a different insertion depth or at predetermined different relative positions.

A preferred massage device according to the invention has a stopping device, by means of which at least one first element can be held or stopped in a predetermined relative position with respect to at least one second element.

Particularly preferably, at least one second element can be clamped with respect to at least one first element or within at least one first element in at least one predetermined relative position between these elements.

Particularly preferably, the massage device can be actuated manually. Preferably, the massage device can be actuated mechanically. Particularly preferably, the massage device can be actuated non-electrically.

Preferably, at least one massage characteristic feature can be adjusted independently of the level or the course with respect to time of the energy or the force which is initiated in the massage device on massaging. The massage action can be adjusted by means of the massage device according to the invention in particular such that a different massage action exists or a different massage action can be felt sensitively when the massage device is supplied optionally manually with a predetermined energy or force and the adjusting device is set in various adjustment positions.

A packing means according to the invention is constructed such that the massage device according to the invention is arranged as the container lid.

Particularly preferably, the invention provides that a massage device according to the invention is provided on a container which is constructed as a shower gel bottle or shampoo bottle or as a soap container, or on another bottle or another container for accommodation of fluids or on a container for accommodation of solid or gaseous substances.

A particular advantage of this packing is that cleaning of the massage body is easy to carry out since an unimpeded passage of water through the guide body is ensured due to the specific construction. As a result, a high preservative concentration in the cleaning composition can be dispensed with. The microbiological safety of the product is also ensured in this manner.

The specific construction of the massage body renders possible pure pressure massage, and skin irritation by excess friction on the skin surface is thus prevented. A very gentle use of the cleaning composition occurs in this manner. The skin is irritated less by the use of a cleaning composition during a massage.

In the context of the invention, a round, angled massage head is used and the massage is thereby simplified considerably. The massage head is preferably oval and designed in a specific concentric arrangement.

Valve systems which are suitable as the valve system according to the invention are those for metered discharge of a substance from a container, a release opening through at least one of the walls of the container being provided for discharge of the substance from the container and a venting opening through at least one of the walls of the container being provided for re-venting; with a first valve which seals off the release opening for the substance as long as a pressure difference between the inside of the container and the outside of the container is smaller than a first predetermined limit value, and which opens the release opening for the substance when the pressure difference between the inside of the container and the outside of the container is greater than the first predetermined limit value, and with a second valve which opens the venting opening for the re-venting as long as a pressure difference between the inside of the container and the outside of the container is smaller than a second predetermined limit value, and which seals off the venting opening for the re-venting when the pressure difference between the insider of the container and the outside of the container is greater than the second predetermined limit value, characterized in that the second valve is made of a flexible material and is constructed in the form of a lip which is capable of closing the venting opening.

According to the invention, the re-venting opening in the first valve and/or the second valve is integrated into the first valve. According to the invention, at least one of the valves is made of a flexible material and is constructed in the form of a lip which is capable of lying over an opening to seal it off.

The inventive container is to be illustrated in the following by some figures, without the intention being an unnecessary limitation by the choice of the examples in the figures.

FIG. 1 shows a specific embodiment of the massage container according to the invention. It substantially comprises seven parts, six parts of which form the massage pin device (2) as an exploded drawing.

The bottle (1), which serves as the product container, is closed by a two-part cap —parts (22) and (23)—with an angle piece (24) on the inside. The bottle (1), produced by the extrusion blow molding process, is substantially of rectangular construction, the edges of the bottle (1) being rounded off. The bottle has at its end of the bottle neck (11) a thread (12) which is capable of forming a firm screw connection with the thread (241) of the angle piece. The second side of the angle piece also has a thread attachment (242) on to which the adjustable part of the massage pin device—the massage pin inner part (25)—is screwed. The massage pin outer part (26) is pushed on to this arrangement, the carrier (621) of the massage pin sieve plate (262) snapping into the recesses (253) of the massage pin inner part (25). At the same time, in the region of the rotating ring (2622) a sliding connection is established with the lower and upper head cap in the region (2623 in FIG. 2). Rotation of the ring leads to movement of the massage pin inner part perpendicularly to the direction of rotation and therefore to moving in and out of the rigid pins (254) into and out of the hollow massage pins (2611), which results in a change in the massage action.

The user of the contents of the bottle (1) can remove a part of the contents through the valve sitting in the region (243) by gentle pressure on the bottle (1) and apply it to his skin, for example. By means of the massage device he can now massage the contents applied into the skin conveniently without having to grasp or seek an additional apparatus.

Figure 2:
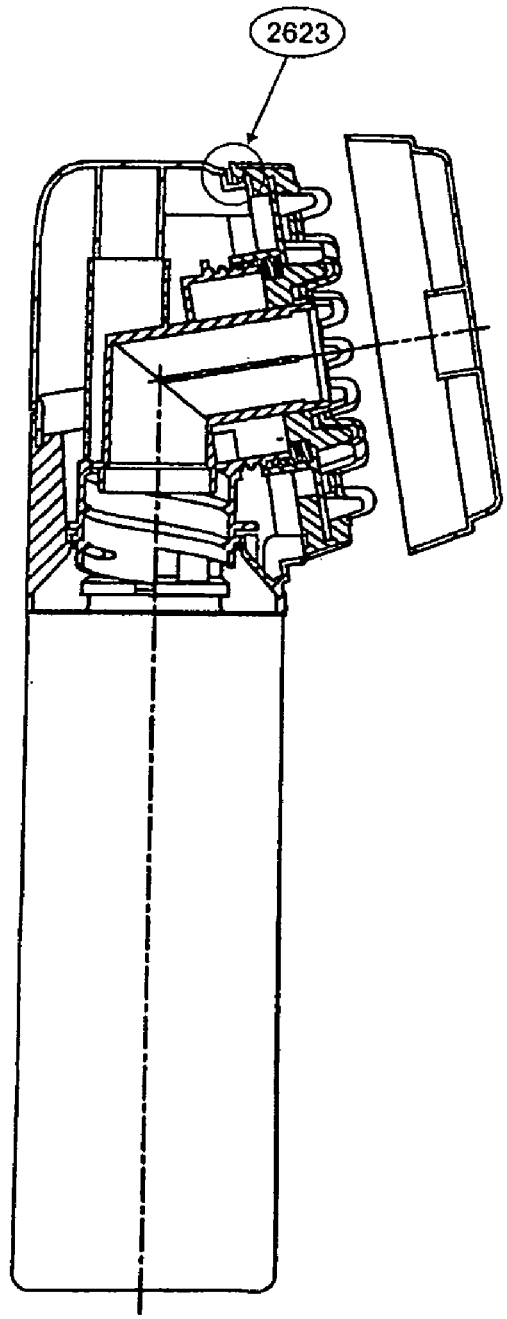
FIG. 2 shows a section through a particularly advantageous embodiment of the massage applicator according to the invention composed of the individual parts shown in FIG. 1, with a particularly advantageous embodiment of a container in bottle form and mounted massage device formed from several devices, in side view.

FIG. 2 shows the massage applicator from FIG. 1 in its assembled form for better understanding.

The invention is not intended to be limited by the embodiments given by way of example and preferred.

The use of the packing means described above in connection with cosmetic or dermatological formulations in the form of gels, emulsions, microemulsions, suspensions, dispersions, colloids, dusting powders, powders and/or pastes also forms part of the invention.

The combination of the container according to the invention with liquid cosmetic cleaning compositions which can be used for massaging cleaning by means of the specific container is particularly advantageous.

The liquid cosmetic cleaning compositions include all formulations with anionic, cationic, nonionic and amphoteric or zwitterionic surfactants.

According to the invention, these formulations can comprise skin care substances. Re-oiling agents, conditioners, peeling bodies or active compounds can be employed as skin care substances.

By the use of a specific shower product with a matched applicator, all the abovementioned points have been improved decisively.

By the use of a shower gel bottle with an integrated massage attachment, it is ensured that the product and massage applicator are matched well to one another and inappropriate use by the user is therefore ruled out. The massage applicator and shower product are matched to one another such that an optimum massage effect is achieved.

The viscosity of the shower formulation is matched to this use in a targeted manner and the slip properties of the formulation on the skin are also optimized. The user therefore achieves an optimum massage effect which is gentle on the skin.

By the fact that the massage applicator and shower product container are firmly connected to one another or cannot easily be separated, the risk of microbial contamination is minimized.

At the same time, by a correspondingly technical embodiment of the bottle and or of the applicator (e.g. with a valve), it is ensured that no foreign substances, such as, for example, water or skin particles, can enter into the packing means.

Hazardous microbial contamination of the filling is therefore prevented. A high concentration of preservatives in the filling can be dispensed with in this manner, which benefits the tolerability of the product.

Preservatives are known among dermatologists for their allergy-inducing and skin-damaging action. The tolerability of this product can be improved considerably by leaving out preservatives. This is particularly important in this form of application—shower with massage—since the product remains on the skin considerably longer due to the massage. The longer duration of application favors the occurrence of irritation by preservatives and wash-active substances.

In addition to the advantages already described, the containers according to the invention have an additional advantage for the user in the field of body care on the basis of the massage effect caused by the changed surface. During application of cosmetic or dermatological formulations a positive effect can simultaneously be achieved, for example for tightening of the skin or against cellulitis.

The shower formulation is chosen such that cleaning of the applicator after use is possible without problems.

At the same time, the valve in the applicator decisively improves the metering of the shower product during use (massage).

If the applicator is constructed in a manner such that the massage intensity is variable, massage of even sensitive parts of the body is possible.

The following examples, in which wash preparations for cleaning the hair and body are described and for which the inventive container can be used in an outstanding manner, are intended to explain the compositions according to the invention, but without the intention being to limit the invention to these examples. The numerical values in the examples denote percentages by weight, based on the total weight of the particular formulation.

EXAMPLE 1

| Sodium laureth sulphate | 11% |
| Cocoamidopropylbetaine | 2.5% |
| Sodium cocoylglutamate | 1.5% |
| PEG-40 hydrogenated castor oil | 0.5% |
| PEG-100 hydrogenated glyceryl palmitate | 0.5% |
| Sodium benzoate | 0.45% |
| Sodium salicylate | 0.2% |
| Citric acid | 0.5% |
| Perfume | q.s. |
| Water | to 100 |

In addition also the following further raw materials: pearlescent waxes (1% to 3%), opacifying agent (waxes or polymers) (0.5% to 3%), polyquaternium-10 (0.1% to 0.3%), and trisodium EDTA (0.2% to 0.6%).

This formulation is distinguished by an extremely reduced adsorption of lauryl ether-sulphate on the skin, this being known for its skin-irritating action. This recipe is therefore very suitable for the application form according to the invention.

EXAMPLE 2

| Sodium myreth sulphate | 4% |
| Sodium laureth sulphate | 3% |
| Cocoamidopropylbetaine | 2% |
| Sodium cocoylglutamate | 2% |
| PEG-40 hydrogenated castor oil | 0.5% |
| PEG-100 hydrogenated glyceryl palmitate | 1.5% |
| Sodium benzoate | 0.45% |
| Sodium salicylate | 0.2% |
| Citric acid | 0.5% |
| Perfume | q.s. |
| Water | to 100 |

In addition also the following further raw materials: pearlescent waxes (1% to 3%), opacifying agent (waxes or polymers) (0.5% to 3%), polyquaternium-10 (0.1% to 0.3%), and trisodium EDTA (0.2% to 0.6%).

In this formulation the -skin tolerability of the recipe under example 1 was improved once more by the use of milder surfactants (e.g. sodium myreth sulphate) and the reduction in the total surfactant concentration.

EXAMPLE 3

| Sodium laureth sulphate | 11% |
| Cocoamidopropylbetaine | 4.3% |
| Sodium lauroyl sarcosinate | 2% |
| PEG-40 hydrogenated castor oil | 0.5% |
| PEG-100 hydrogenated glyceryl palmitate | 1.5% |
| Sodium benzoate | 0.45% |
| Sodium salicylate | 0.2% |
| Citric acid | 0.5% |
| PEG-4 rape seed amide | 4% |
| PEG-9 cocoglycerides | 1.6% |
| Hydroxypropyl guarhydroxypropyltrimonium chloride | 0.3% |
| Perfume | q.s. |
| Water | to 100 |

By the use of skin care substances and moisturzers (e.g. PEG-4 rape seed amide and PEG-9 cocoglyceride), this formulation is suitable specifically for the use of a massage shower.

By massage with the shower product according to the invention, these skin care substances can display their action to the optimum. Their action can additionally be increased considerably.

EXAMPLE 4

| Decyl glucoside | 11% |
| Carbopol 1382 | 1.2% |
| Sodium hydroxide | 0.5% |
| Butylene glycol | 9% |
| Propylene glycol | 18% |
| Na$_3$H EDTA | 0.5% |
| Sodium benzoate | 0.3% |
| Sodium salicylate | 0.2% |
| Perfume | q.s. |
| Water | to 100 |

By the use of only nonionic surfactants, the formula is particularly skin-friendly. In addition, the use of gel-forming agents considerably improves the slip properties of the massage head when this product is used. Both effects are of advantage for use as a massage shower.

EXAMPLE 5

| | |
|---|---|
| Paraffin oil | 25% |
| Soya oil | 25% |
| Sodium lauryl ether-sulphate | 9% |
| Sodium benzoate | 0.3% |
| Sodium salicylate | 0.2% |
| Acrylates/C10-C30 alkyl acrylate cross polymer | 2% |
| Sodium hydroxide | 0.2% |
| Phenoxyethanol | 0.3% |
| Parabens | 0.1% |
| Perfume | q.s. |
| Water | to 100 |

The use of gel-forming agents improves the slip properties of the massage head considerably when this product is used. The high content of skin care oils already allows an active re-oiling during massage. The skin care oils are massaged into the upper layers of skin by this application form, as a result of which their activity is improved.

EXAMPLE 6

| | |
|---|---|
| Soya oil | 40% |
| Castor oil | 15% |
| Sunflower oil | — |
| Wheat germ oil | — |
| Zetesol 100 | 40% |
| Poloxamer 101 | 2% |
| Perfume, antioxidants, preservatives | q.s. |
| Water | to 100 |

By the considerable oil content in this formulation compared with example 5, during use an increased re-oiling occurs when used. As a result massage-related irritation is prevented.

EXAMPLE 7

| | |
|---|---|
| Sodium laureth sulphate | 11% |
| Sodium cocoamphoacetate | 4% |
| Polyethylene | 4% |
| Sodium cocoylglutamate | 1% |
| PEG-40 glyceryl cocoate | 0.5% |
| Phenoxyethanol + methyldibromo glutaronitrile | 0.2% |
| Hydroxypropyl guarhydroxypropyltrimonium chloride | 0.1% |
| PEG-3 distearate | 2% |
| Magnesium aluminum silicate | 2.5% |
| Citric acid | 0.5% |
| Perfume | q.s. |
| Water | to 100 |

By the use of peeling particles, an intensification of the massage action occurs with this formulation.

That which is claimed:

1. A cosmetic cleaning product, comprising:
a massage applicator comprising
a container body and
a massage device having (a) at least one massage pin device, said pin device having at least one first surface which is configured to be in contact with the surface to be massaged, wherein a force can be transmitted between the first surface of the massage pin device and the surface to be massaged, and wherein at least one predetermined massage characteristic feature selected from the group consisting of a predetermined hardness, a predetermined geometry and a predetermined elasticity exists in a region of the first surface of the massage pin device which is configured to be in contact with the surface to be massaged, and (b) at least one adjusting device which can adjust said at least one predetermined massage characteristic feature, and
a cosmetic cleaning formulation.

2. The cleaning product as claimed in claim 1, wherein the predetermined massage characteristic feature can be adjusted by turning, horizontal or vertical displacement of an interior component.

3. The cleaning product as claimed in claim 2, wherein the predetermined massage characteristic feature is infinitely adjustable.

4. The cleaning product as claimed in claim 2, wherein the predetermined massage characteristic feature is the hardness.

5. The cleaning product as claimed in claim 2, wherein the predetermined massage characteristic feature is the geometry.

6. The cleaning product as claimed in claim 2, wherein the predetermined massage characteristic feature is the elasticity.

7. The cleaning product as claimed in claim 1, wherein at least a portion of the massage applicator is produced from plastic.

8. The cleaning product as claimed in claim 7, wherein the plastic includes polyethylene or polypropylene.

9. The cleaning product as claimed in claim 1, wherein the massage device further comprises a stopping device configured such that at least one first element can be stopped in a predetermined relative position with respect to at least one second element.

10. The cleaning product as claimed in claim 1, wherein said massage pin device comprises a plurality of massage pins arranged in a geometric pattern.

11. The cleaning product as claimed in claim 10, wherein said plurality of massage pins is arranged concentrically.

12. The cleaning product as claimed in claim 10, wherein said massage pins are oval.

13. The cleaning product as claimed in claim 1, wherein the massage device is round and angled.

14. The cleaning product as claimed in claim 1, wherein the massage device can be transferred to new container bodies for re-use.

15. The cleaning product as claimed in claim 1, wherein the container body is separated from the massage device by a valve.

16. The cleaning product as claimed in claim 1, wherein viscosity and slip properties of the cosmetic cleaning formulation are matched to the properties of the massage device.

17. The cleaning product as claimed in claim 1, wherein the cleaning formulation is in a form selected from the group consisting of gels, emulsions, microemulsions, suspensions, dispersions, colloids, dusting powders, powders and pastes.

18. The cleaning product as claimed in claim 1, wherein the cleaning formulation comprises one or more surfactants selected from the group consisting of anionic, cationic, nonionic, amphoteric and zwitterionic surfactants.

19. The cleaning product as claimed in claim 18, wherein the cleaning formulation further comprises anionic cocoylglutamate.

20. The cleaning product as claimed in claim 18, wherein the cleaning formulation further comprises ethoxylated fatty acid derivatives.

21. The cleaning product as claimed in claim 18, further comprising one or more of triglycerides and mineral oils.

22. The cleaning product as claimed in claim 18, further comprising peeling bodies of organic or synthetic materials for rubbing off the upper layers of the stratum corneum.

23. A shower product comprising the cosmetic cleaning product of claim 1.

24. A cosmetic product, comprising:
 a massage applicator comprising:
  a container body for containing a cosmetic or dermatological formulation; and
  a massage device for massaging a surface, said massage device being attached to the container body, wherein said massage device comprises:
   (a) at least one outer massage pin having a hollow construction and an outer surface formed to be in contact with the surface to be massaged and formed to transmit a force between the outer surface of the at least one outer massage pin and the surface to be massaged such that at least one predetermined massage characteristic is provided by the at least one outer massage pin to the surface to be massaged; and
   (b) at least one inner massage pin capable of adjusting the at least one predetermined massage characteristic of the at least one outer massage pin; and
 a cosmetic or dermatological formulation.

* * * * *